US006846289B2

(12) United States Patent
Besson et al.

(10) Patent No.: US 6,846,289 B2
(45) Date of Patent: Jan. 25, 2005

(54) INTEGRATED X-RAY AND ULTRASOUND MEDICAL IMAGING SYSTEM

(75) Inventors: Guy M. Besson, Broomfield, CO (US); Morgan W. Nields, Englewood, CO (US)

(73) Assignee: Fischer Imaging Corporation, Denver, CO (US)

(*) Notice: Subject to any disclaimer, the term of this patent is extended or adjusted under 35 U.S.C. 154(b) by 29 days.

(21) Appl. No.: 10/455,878

(22) Filed: Jun. 6, 2003

(65) Prior Publication Data

US 2004/0249271 A1 Dec. 9, 2004

(51) Int. Cl.⁷ .............................................. A61B 8/00
(52) U.S. Cl. ................................................... 600/437
(58) Field of Search ......................... 600/407–472; 73/595–633; 367/7, 11, 130, 138; 128/916

(56) References Cited

U.S. PATENT DOCUMENTS

| | | | |
|---|---|---|---|
| 4,969,174 A | 11/1990 | Scheid et al. | 378/146 |
| 5,474,072 A | 12/1995 | Shmulewitz | 128/660.09 |
| 5,526,394 A | 6/1996 | Siczek et al. | 378/37 |
| 5,630,426 A | 5/1997 | Eggers et al. | 128/734 |
| 5,640,956 A | 6/1997 | Getzinger et al. | 128/653.1 |
| 5,660,185 A | 8/1997 | Shmulewitz et al. | 128/749 |
| 5,664,573 A | 9/1997 | Shmulewitz | 128/660.09 |
| 5,776,062 A | 7/1998 | Nields | 600/407 |
| 5,851,180 A | 12/1998 | Crosby et al. | 600/407 |
| 5,917,881 A | 6/1999 | Jeffery | 378/98.8 |
| 5,938,613 A | 8/1999 | Shmulewitz | 600/461 |
| 5,979,457 A | 11/1999 | Rohrberg | 128/915 |
| 5,984,870 A | 11/1999 | Giger et al. | 600/443 |
| 6,027,457 A | 2/2000 | Shmulewitz et al. | 600/562 |
| 6,385,474 B1 | 5/2002 | Rather et al. | 600/407 |
| 6,396,940 B1 | 5/2002 | Carrott et al. | 382/128 |
| 6,421,454 B1 | 7/2002 | Burke et al. | 382/131 |
| 6,459,925 B1 | 10/2002 | Nields et al. | 600/427 |
| 6,483,891 B1 | 11/2002 | Lazarev et al. | 378/37 |
| 6,524,246 B1 | 2/2003 | Kelly et al. | 600/437 |
| 6,574,499 B1 | 6/2003 | Dines et al. | 600/427 |

*Primary Examiner*—Ali Imam
(74) *Attorney, Agent, or Firm*—Marsh Fischmann & Breyfogle LLP

(57) ABSTRACT

An integrated x-ray and ultrasound medical imaging system is provided, wherein a radiation detection means and ultrasound transducer may be disposed for scanning movement for image acquisition along either the same or substantially coincidental paths. The radiation detection means and ultrasound transducer may be advantageously located on the same side of the imaged body portion. The x-ray and ultrasound imaging operations may be sequential, partially overlapping, or synchronous. By virtue of the noted arrangement, increased accuracy and medical efficiencies can be realized.

28 Claims, 8 Drawing Sheets

INTEGRATED X-RAY AND ULTRASOUND MEDICAL IMAGING SYSTEM

FIELD OF THE INVENTION

The present invention relates to medical imaging systems, and more particularly, to an improved system that combinatively employs x-ray imaging and ultrasound imaging in a manner that yields enhanced accuracy and multiple efficiencies.

BACKGROUND OF THE INVENTION

The advantages of early detection of potential lesions and suspicious masses within bodily tissue have been well-established. Increasingly, screening for common cancers of the breast, lung, colon, and prostate has gained support and acceptance in the medical community, but improvements in the sensitivity and specificity of the techniques remain key and are readily identifiable objectives.

Of particular interest is the area of mammographic screening. After a given age or maturity, normally beginning at age 40, it is common for women to undergo periodic examinations, wherein film-based and/or digital x-ray screening mammograms are obtained. While significant advances have been made, current screening approaches may provide mammograms with insufficient "sensitivity" to allow for the detection of the presence of a potential lesion, thereby resulting in a "false negative". Further, current screening approaches may provide mammograms with insufficient "specificity" to allow for accurate characterization of detected suspicion tissue masses, thereby potentially resulting in "false positives".

Presently, in the event of an equivocal screening mammogram, a callback examination may be conducted, wherein a diagnostic mammogram is obtained and/or an ultrasound imaging procedure is performed, thereby entailing another patient office visit, additional medical personnel time and increased cost. More particularly, an ultrasound examination may be utilized (e.g. as opposed to a biopsy) to rule out the presence of a solid mass. In this regard, current practice can entail free-hand ultrasound imaging during which a specialist manipulates a hand-held probe relative to a patient's breast while viewing a display to obtain depth-profile information. As may be appreciated, the ability to mentally correlate such depth-profile information with the location of a potential lesion/suspicious mass visualized on an x-ray image can be quite challenging, thereby sometimes compromising characterization efforts. Moreover, such procedures are time consuming and entail significant expertise. These considerations present significant limitations to the realization of increased efficacies and efficiencies of practice.

SUMMARY OF THE INVENTION

In view of the foregoing, a primary objective of the present invention is to provide a medical imaging system that reduces instances of undetected malignancies (e.g. false negatives) and/or falsely characterized non-malignancies (e.g. false positives) by providing increased sensitivity and specificity.

Another objective of the present invention is to provide a medical imaging system that reduces the need of callbacks for patients undergoing screening examinations.

Yet another objective of the present invention is to provide a medical imaging system that improves overall efficiencies in the delivery of medical screening services.

A further objective of the present invention is to provide a medical imaging system that is patient and user-friendly in implementation, including in particular patient screening applications.

One or more of the above objectives and additional advantages are realized by the present invention. An inventive apparatus includes a radiation source for transmitting a radiation signal through a selected region of a patient's body, and a radiation detection means for receiving a portion of the radiation signal passing through the selected body region and providing a first image signal responsive thereto. Further, the apparatus includes at least one ultrasound transducer for sending/receiving an ultrasound signal into/from the selected region of the patient's body and providing a second image signal responsive thereto. The radiation detection means and ultrasound transducer may be disposed in known spatial relation to a predetermined imaging frame of reference in which the selected body region may be immobilized, wherein the first and second image signals may be readily correlated and otherwise processed for the generation and display of images to medical personnel (e.g. specialists located at a patient screening site or a networked location).

More particularly, and in one aspect, the inventive apparatus may be provided so that the radiation detection means and ultrasound transducer are each operable for scanning movement relative to the selected body region along the same or substantially coincidental paths during image acquisition (e.g. parallel, linear or arcuate paths). In this regard, the radiation detection means and ultrasound transducer may each be of a width that is less than a width of the selected body region, wherein the noted scanning movement allows the entirety of the selected body region to be progressively, or incrementally, imaged with enhanced results. For example, the radiation signal may be substantially focused upon and scanned in synchronous relation with the radiation detection means to reduce scattering effects and otherwise yield high detection quantum efficiencies. Relatedly, it may be preferable for one or both of the radiation detection means and ultrasound transducer to have corresponding lengths that are at least as great as the length of the selected body region. In turn, image acquisition for the entire selected body region may be achieved via a single scanning movement, or pass, of the radiation detection means and/or ultrasound transducer across the width of selected body region, wherein temporal decorrelation effects may be reduced. Alternatively, one or both of the radiation detection means and ultrasound transducer may be of a length that is less than the length of the selected body region, wherein a plurality of scanning movements along parallel paths may be utilized (e.g. via raster, bi-directional or return carriage, unidirectional imaging arrangements).

The radiation detection means may comprise an array of radiation detector elements and the ultrasound transducer may comprise an array of ultrasound transducer elements, wherein each of the arrays are positioned or positionable in known spatial relation relative to the imaging frame of reference. Further, the array of radiation detector elements and array of ultrasound transducer elements may be positioned or positionable so that the row(s)/column(s) thereof are disposed in a like relationship relative to their respective scanning travel paths. For example, the element row(s) of each of the arrays may be oriented substantially perpendicular to their corresponding scanning travel paths and the element column(s) of each of the arrays may be oriented substantially parallel to their corresponding scanning travel paths, wherein such scanning travel paths are the same or substantially coincidental.

To effect scanning movement, the radiation detection means and ultrasound transducer may be operably interconnected to a common or separate corresponding drive means (e.g. one or more stepper motor(s)) for moving the radiation detection means and ultrasound transducer in a controlled manner relative to the predetermined imaging frame of reference. Preferably, the drive means may be provided so that the radiation detection means and ultrasound transducer may each be scanned at corresponding predetermined and substantially constant velocities, wherein such velocities may be the same or different. For example, the detection means and ultrasound transducer may be driven for at least partially synchronous scanning, preferably at substantially the same, constant velocity. Alternatively, radiation and ultrasound scanning may be conducted sequentially at the same or different corresponding velocities as may be desired due to varying acquisition system bandwidths.

The radiation source and radiation detection means may be provided to maintain a substantially fixed distance therebetween throughout scanning. In this regard, the radiation source may be rotatable about and have a focal point located on a substantially fixed axis, and the radiation detection means may be disposed for movement along an arcuate path centered at the focal point of the radiation source during imaging. Further, the ultrasound transducer may also be provided for movement along a coincidental, arcuate path or along a linear path during imaging.

In another aspect, the inventive apparatus may be provided so that the ultrasound transducer is disposed for scanning co-movement with and in fixed relation to the radiation detection means. In this regard, the radiation detection means and ultrasound transducer may be physically interconnected or interconnectable. For example, one of the radiation detection means and ultrasound transducer may be supportably carried by the other, wherein the carrier is supportably interconnected to a drive means. Alternatively, the radiation detector and ultrasound transducer may each be interconnected or interconnectable in known spatial relation to a common support member.

According to a further aspect of the present invention, the inventive apparatus may be provided so that a selected region of the patient's body is positionable with (i.) the radiation source on a first side thereof, and (ii.) the radiation detection means and ultrasound transducer on an opposing, second side thereof. In one arrangement, the selected body region may be located in contact relation with a first side of a support layer, wherein the radiation detection means and ultrasound transducer are located or locatable on an opposing second side of the support layer for imaging through the support layer. As may be appreciated, the support layer should be both radiolucent and sonolucent to accommodate the passage of x-ray and ultrasound imaging signals therethrough. Further, an acoustic coupling means may be positioned or positionable in contact relation with both the ultrasound transducer and the second side of the support layer. For example, the acoustic coupling means may be sonolucent and flowable (e.g. conformable) to facilitate an acoustic interface between the ultrasound transducer and support layer.

The support layer may be of an arcuate or planar (e.g. flat) configuration and may be of rigid or pliable construction. In turn, to facilitate the maintenance of a contact relationship between the ultrasound transducer, acoustic coupling means, support layer and selected body region, the ultrasound transducer may be disposed for scanning movement along a travel path that substantially coincides with the shape of the support layer (e.g. a coincidental arcuate or linear path).

Additionally, to facilitate contact maintenance, the ultrasound transducer may be disposed for movement toward and away from the second side of the support layer during scanning movement. For example, the ultrasound transducer may be biased toward the support layer (e.g. spring-loaded along a slot mount in a support bracket). Further, the ultrasound transducer may be disposed to permit the pitch and/or attitude of the ultrasound transducer (e.g. relative to the support layer) to automatically adjust in response to local shape variations (e.g. variations caused by local tissue variations of a compressed breast deforming a pliable support member). For example, an ultrasound transducer may be mounted to a support bracket via a ball-joint or gimbal arrangement.

In yet a further aspect of the present invention, the inventive apparatus may include a processor means for controlling operation of the radiation source, radiation detection means, ultrasound transducer and scanning drive means. More particularly, the processor means may control the drive means to effect scanning movement of and imaging operations by the radiation detection means and ultrasound transducer in a sequential, partially overlapping or substantially synchronous manner.

Various embodiments of the inventive apparatus may employ one or more of the above-noted aspects and further additional features. Of note, the inventive apparatus may include a user interface means for displaying a plurality of images of the selected body region that are generated by the processor means utilizing image data obtained from the first and/or second image signals. More particularly, the user interface means may include a display and a user input for controlling the processor means, wherein a first image may be displayed and utilized to select at least a second image. For example, a user input (e.g. a mouse) may be provided to control positioning of a cursor relative to a region of interest on a displayed projection image generated from the x-ray image data (e.g. a projected XY plane image), wherein upon locating the cursor and corresponding user input (e.g. via clicking a mouse button), corresponding cross-cut, z-depth plane images may be generated by the processor means from the ultrasound image dataset and displayed to a user (e.g. YZ and XZ plane images extending through the region of interest). Further, the cursor may be positioned relative to a region of interest on one of the YZ or XZ plane images to obtain a desired XY plane image at a selected Z elevation, wherein such image is generated by the processor means from the ultrasound image dataset. As may be appreciated, the ultrasound image dataset may also be utilized to generate three-dimensional images of a region of interest.

In other embodiments a pair of ultrasound transducers may be utilized. For example, a first ultrasound transducer may be disposed on a first side of the selected body region and a second ultrasound transducer may be located on an opposing, second side of the selected body region, wherein the first and second ultrasound transducers are preferably disposed in opposing, aligned relation. More particularly, the first ultrasound transducer may be disposed in contact relation with first acoustic coupling means which is disposed in contact relation with a support layer as described hereinabove. The second ultrasound transducer may be disposed in direction contact with a second acoustic coupling means that is disposed in contact relation with a compression member, wherein the selected body region is immobilized in contact relation between the support layer and the compression member. The utilization of a pair of ultrasound transducer allows for the obtainment of various tissue properties corresponding with the selected body region. For example, an ultrasound signal may be transmitted by the first ultrasound transducer and received by the second ultrasound transducer to yield tissue attenuation and/or signal velocity information, both of which types of information may be utilized to facilitate characterization of tissue masses within the selected body region.

In yet further embodiments, an ultrasound image dataset obtained via one or a pair of ultrasound transducers may be processed to obtain Doppler image data. In turn, the Doppler image data may be utilized to measure the direction and velocity of blood flow in a tissue region of interest and to provide a visual display thereof (e.g. a color Doppler image).

As may be appreciated, an inventive method is also provided for use in obtaining image data with respect to a selected region of a patient's body. The inventive method includes the steps of transmitting a radiation signal from a radiation source through the selected body region and moving a radiation detection means along a first path during the transmitting step, wherein the radiation detection means receives a portion of the radiation signal passing through the selected body region and provides a first image signal responsive thereto. The method further includes a step of displacing an ultrasound transducer along a second path, wherein the ultrasound transducer sends/receives an ultrasound signal from the selected body region as it travels along said second path and provides a second image signal responsive thereto. The method may further provide for processing the first and second image signals, and for the selective display of resultant images to medical personnel.

In conjunction with the inventive method, the selected body region may be immobilized within a predetermined frame of reference, wherein the transmitting, moving and displacing steps are completed during the immobilization step. Further, the immobilization step may provide for compression of the selected body region.

According to one aspect, the method may entail movement of the radiation detection means and displacement of the ultrasound transducer along corresponding first and second paths which are the same or substantially coincidental (i.e. parallel, linear or arcuate paths). By way of example, the radiation detection means and ultrasound transducer may be directly interconnected or interconnectable or to a common support means for driven movement. Additionally, the transmitting step may include scanning the radiation signal across the selected body region synchronous with and in the same direction as the radiation detection means. Further, the radiation signal may be substantially focused upon the radiation detection means during imaging, wherein radiation dosages are reduced and image resolutions are enhanced.

In another aspect, the inventive method may provide for positioning of the radiation detection means and ultrasound transducer on the same side of a selected body region of the patient. By way of example, a first side of a support layer may be located adjacent to the selected body region, wherein the radiation detection means and ultrasound transducer may be located on an opposing second side of the support layer for scanning movement. To facilitate ultrasound imaging, acoustic coupling means may be utilized on each side of the support layer. For example, an acoustic coupling member (e.g. a conformable pad containing a flowable acoustic gel) may be interposed between and in direct contact with the first side of the support layer and the selected body region.

Further in this regard, an acoustic coupling member (e.g. a conformable pad containing a flowable acoustic gel) may be interposed between the ultrasound transducer and the second side of said support layer in direct contact with each.

By way of example, the acoustic coupling member may be interconnected to the ultrasound transducer, wherein the acoustic coupling member slidably engages the support layer during scanning displacement. Alternatively, the acoustic coupling member may be interconnected to the second side of the support layer, wherein the ultrasound transducer slidably engages the acoustic coupling member during scanning displacement. In such an arrangement, processing of the first image signal may include an adjustment to account for x-ray attenuation associated with the passage of the radiation signal through the acoustic coupling member. In one approach, to facilitate such an adjustment, the inventive method may initially provide for transmission of the radiation signal and movement of the radiation detection means along the first scanning path prior to actual imaging of said selected body region. Concomitantly, the radiation detection means may receive a portion of the radiation signal passing through the acoustic coupling member and provide a calibration output signal responsive thereto. In turn, the calibration signal may be stored/utilized in conjunction with the above-noted image processing adjustment.

To further facilitate ultrasound imaging, an acoustic gel or other ultrasound couplant may be applied to the selected body region to be imaged and/or to the support layer prior to imaging to enhance the acoustic interface therebetween.

In another aspect of the inventive method, scanning movement of the radiation detection means and scanning displacement of the ultrasound transducer for body imaging may occur in at least a partially overlapping manner. For example, the moving and displacing steps for radiation and ultrasound imaging may be completed in substantial synchronicity. In another approach, scanning movement of the radiation detection means and scanning displacement of the ultrasound transducer for body imaging may be completed sequentially.

Additional aspects and advantages of the present invention will become apparent to those skilled in the art upon consideration of the further description provided hereinbelow.

DETAILED DESCRIPTION

Figure 1:
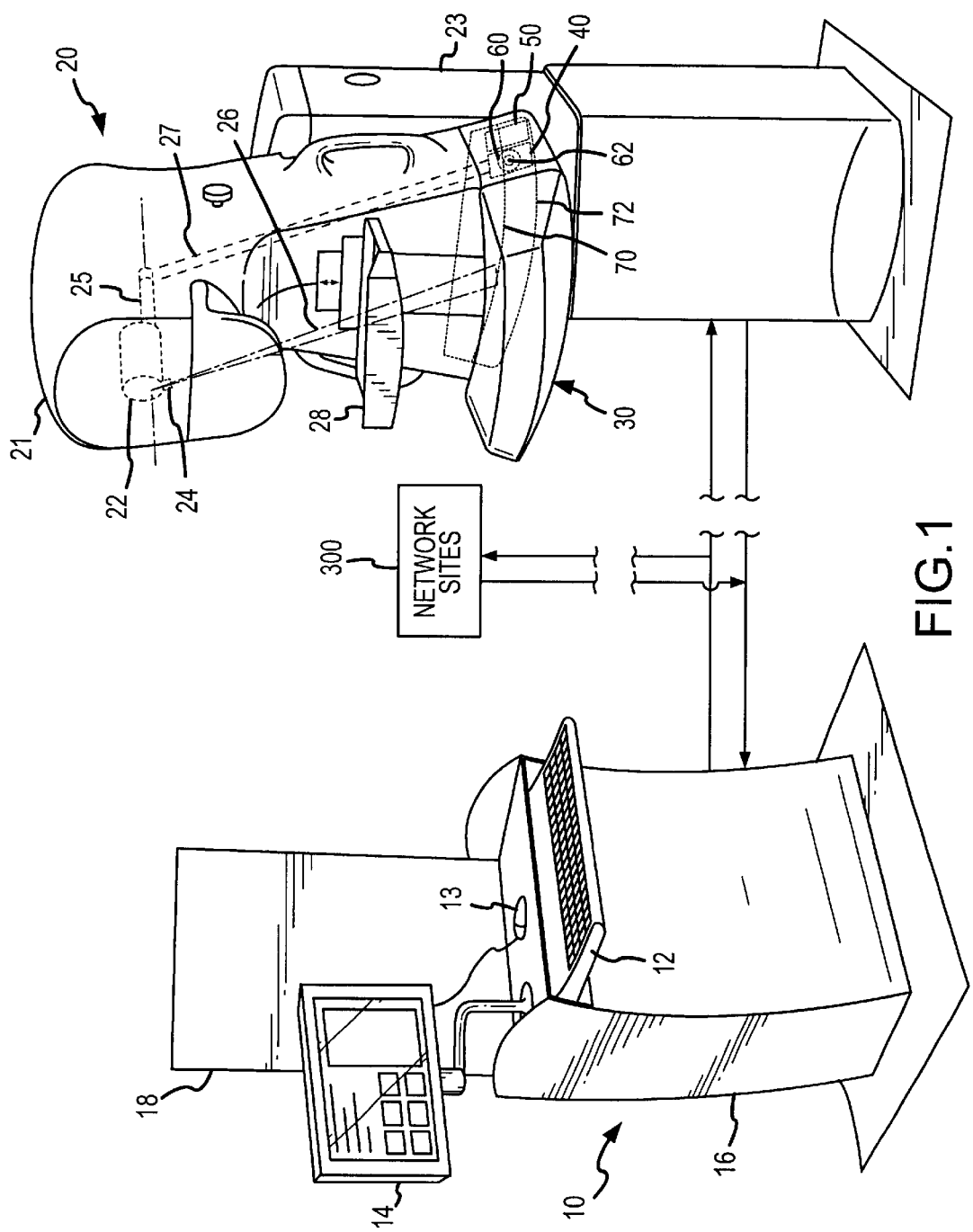
FIG. 1 illustrates one embodiment of an imaging system comprising features of the present invention.

FIG. 1 illustrates one embodiment of an imaging system comprising the present invention. The system includes a monitoring station 10 and imaging station 20 operatively interconnected thereto, e.g. for patient screening and/or follow-up examination. The monitoring station 10 includes a user input keyboard 12 (e.g. for entering patient data), a display 14 and corresponding user input mouse 13 (e.g. for displaying/selecting images), and a processor 16 interconnected to the user input keyboard 12, display 14 and imaging station 20. Processor 16 is adapted to receive, process and store image data comprising image signals generated at the imaging station 20, and to control various operations at the imaging station 20. The monitoring station 10 may also include a radiopaque and optically transparent shield 18 for shielding medical personnel during observed patient imaging operations at the imaging station 20.

The monitoring station 10 and/or imaging station 20 may be further interconnected or interconnectable in a network arrangement with other user workstations and image processor/storage sites 300. For example, image data obtained at imaging station 20 may be provided to a networked location (e.g. at a remote site) for high-resolution display and analysis by diagnostic specialists.

The imaging station 20 may include an x-ray radiation source 22, e.g. an x-ray tube, and collimating optics and/or selectable filters 24, for transmitting a focused radiation signal 26. By way of example, the radiation signal 26 may comprise a fan-shaped beam. The radiation source 22 may be disposed for controlled rotation about a fixed axis, wherein the radiation signal 26 may be scanned across a selected region of a patient's body.

By way of primary example, a patient's breast may be located within a predetermined imaging frame of reference located immediately adjacent to an imaging assembly 30. More particularly, a patient breast may be immobilized between a support layer of the imaging assembly 30 and a compression member 28. The compression member 28 may be selectively raisable/lowerable relative to the imaging assembly 30. Further, the radiation source 22, compression member 28 and imaging assembly 30 may be supportably mounted to an upper station member 21 that is supportably connected to and selectively raisable/lowerable/rotatable relative to a pedestal station member 23. By virtue of such arrangement, the compression member 28 and imaging assembly 30 may be selectively positioned to accommodate varying patient heights, breast sizes and x-ray imaging angles.

As previously noted, radiation signal 26 may be scanned across a selected region of a patient's body, e.g. a patient's breast. In this regard, radiation source 22 may be interconnected to a rotatable shaft 25 (e.g. for co-rotation therewith), wherein a focal point of the radiation source 22 is located on a substantially fixed center axis of the rotatable shaft 25. In turn, a top end of a pendulum member 27 may be interconnected to rotatable shaft 25, wherein the pendulum member 27 may pivot about the center axis of shaft 25 when shaft 25 rotates.

A bottom end the pendulum member 27 may be interconnected to a drive motor 60 (e.g. a stepper motor), and to an x-ray detector 40 and ultrasound imager 50 comprising imaging assembly 30. In this regard, the drive motor 60 may be selectively operated to move the x-ray detector 40 and ultrasound imager 50 along corresponding arcuate scanning travel paths. In the illustrated arrangement, operation of drive motor 60 will also effect synchronized scanning of the radiation signal 26 along a coincidental arcuate path by virtue of the operative interconnection of drive motor 60 to radiation source 22 via pendulum member 27 and shaft 25.

Further in this regard, drive motor 60 may comprise an output shaft 62 that travels along a cam surface 70 of a cam member 72 (e.g. mounted to upper station member 21) upon rotation of the output shaft 62. More particularly, an arrangement may be provided as disclosed in U.S. Pat. No. 5,917,881, entitled "DIGITAL SCAN MAMMOGRAPHY APPARATUS UTILIZING VELOCITY ADAPTIVE FEEDBACK AND METHOD", hereby incorporated by reference, or U.S. Pat. No. 5,526,394, entitled "DIGITAL SCAN MAMMOGRAPHY APPARATUS", hereby incorporated by reference.

Figure 2A:
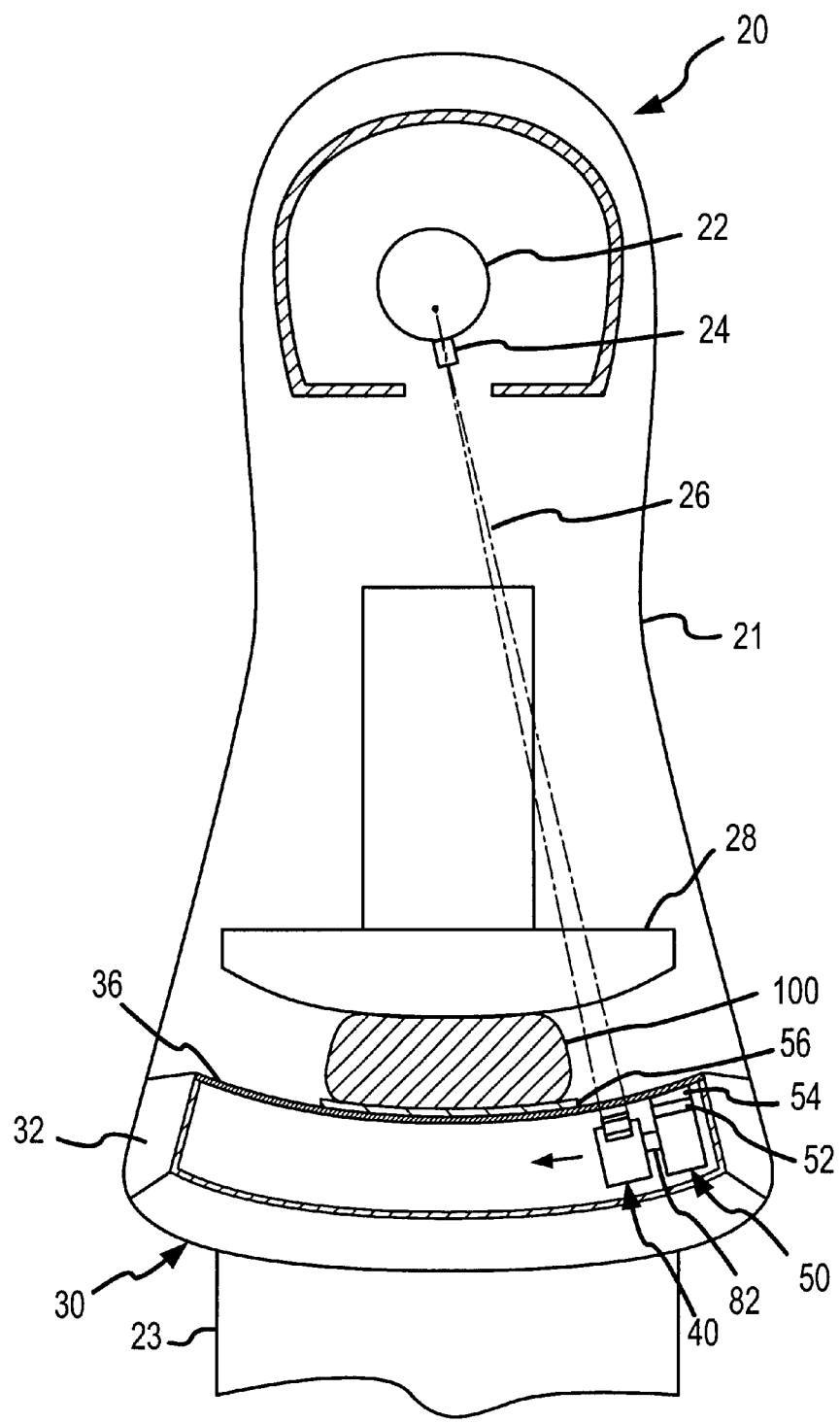
FIGS. 2A–2C are cross-sectional front views of an imaging station of the embodiment of FIG. 1, wherein progressive tandem, scanning movement of an x-ray detector and ultrasound imager is illustrated.
Figure 2B:
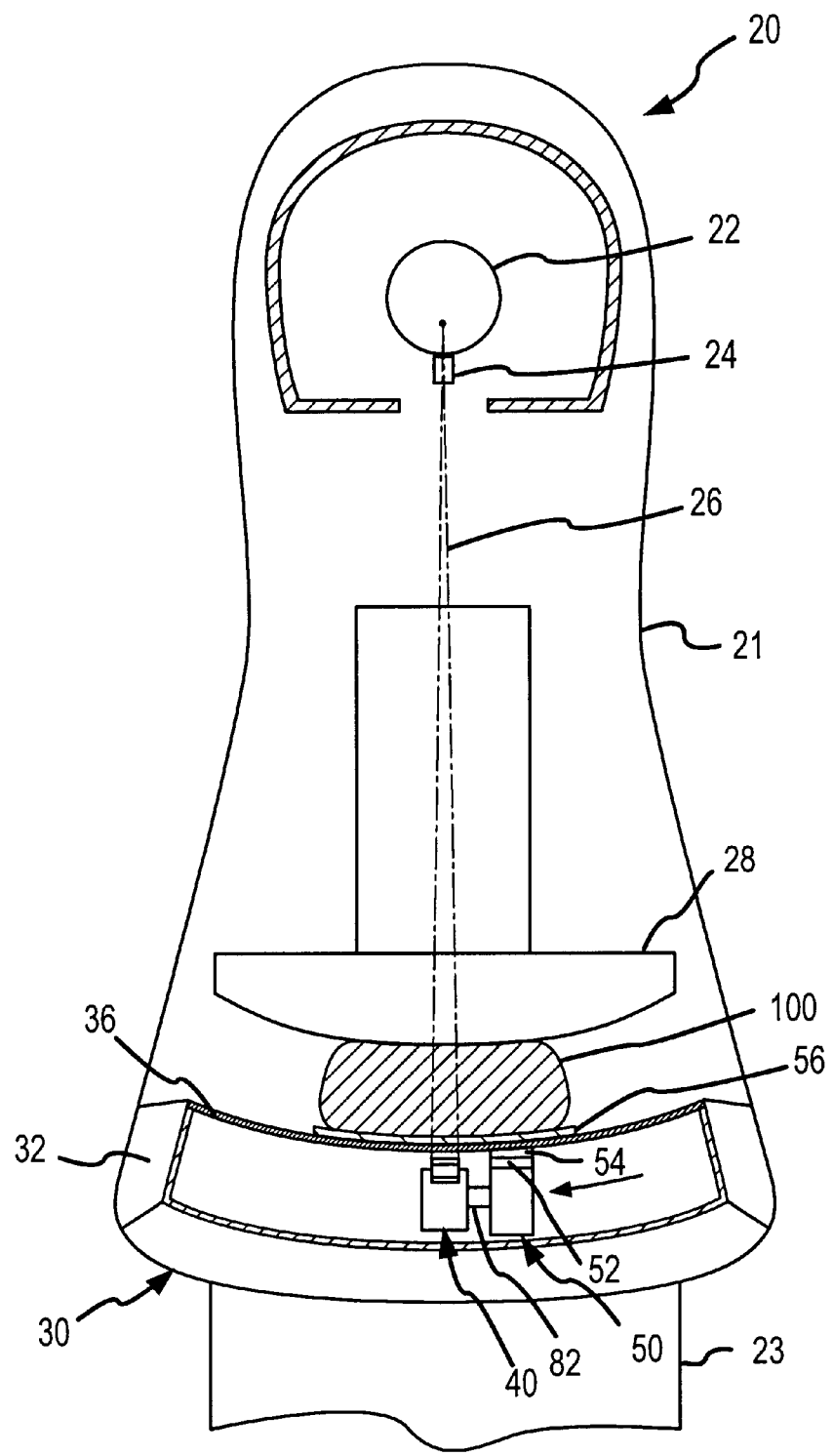
Figure 2C:
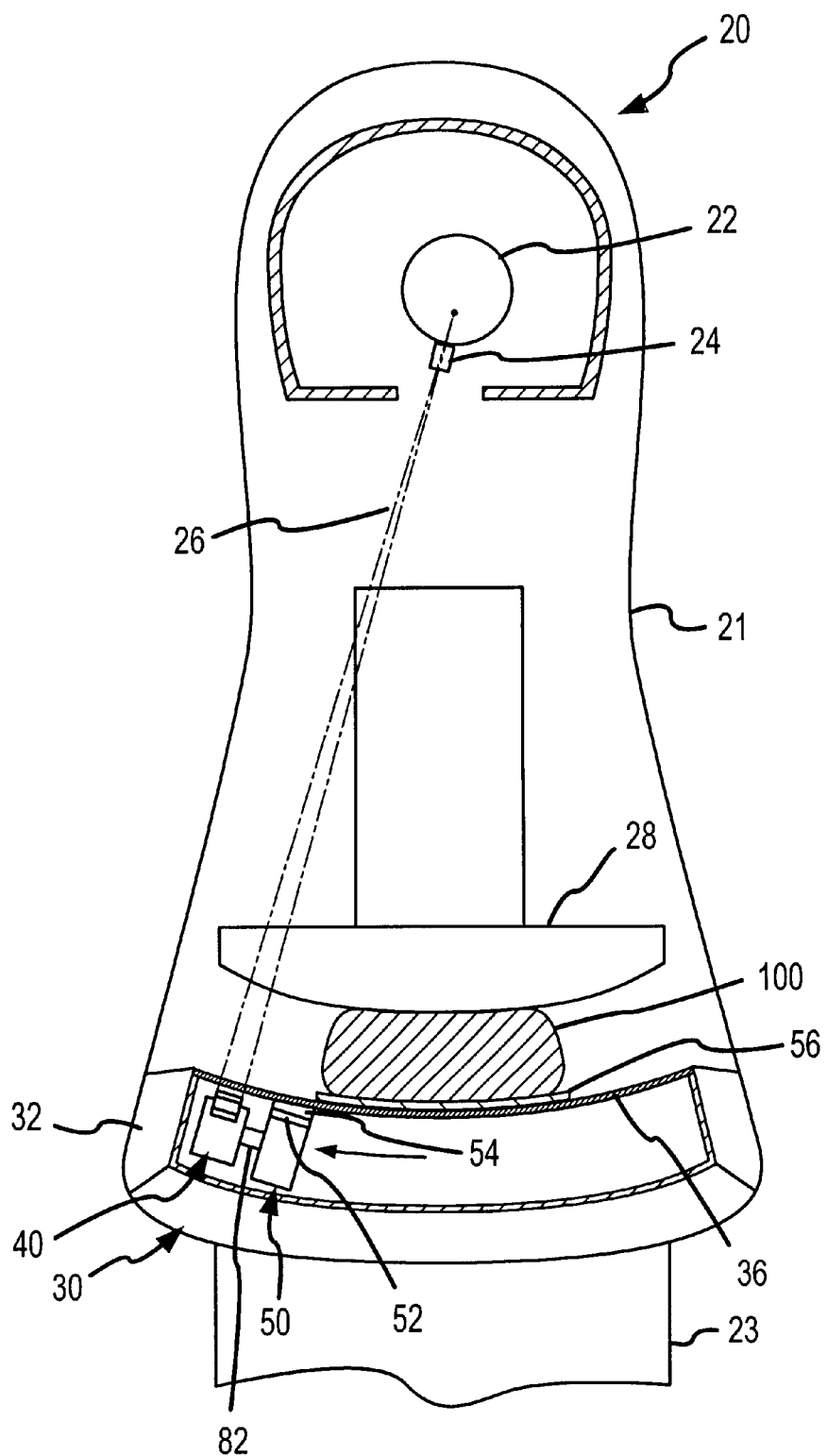

Reference will now be made to FIGS. 2A–2C for further description of the imaging assembly 30, as shown in imaging relation to a patient's breast 100. As noted above, imaging assembly 30 includes an x-ray detector 40 and ultrasound imager 50. The x-ray detector 40 receives at least a portion of the radiation signal 26 passing through a patient's breast 100 and provides a digital x-ray image signal in response thereto.

Ultrasound imager 50 transmits/receives ultrasound signals into/from a patient's breast 100 and provides a digital ultrasound image signal in response thereto.

The x-ray detector 40 and ultrasound imager 50 may be located within a housing 32 having a support layer 36. The x-ray detector 40, ultrasound imager 50 and drive motor 60 may be interconnected to a bracket member (not shown) that is interconnected to the bottom end of the pendulum member 27. As noted, the drive motor 60 may be operated to effect radiation signal 26 scanning and scanning displacement of the x-ray detector 40 and ultrasound imager 50 along the same path or substantially coincidental paths relative to the predetermined imaging frame of reference. In that regard, each of radiation source 22, x-ray detector 40, ultrasound imager 50 and the drive motor 60 may be operatively interconnected (e.g. via electrical and/or optical lines) to the processor 16 at monitoring station 10, wherein control signals are provided by processor 16 and image signals are received at processor 16 from the imaging station 20.

In the embodiment shown in FIGS. 2A–2C, the ultrasound imager 50 and x-ray detector 40 are physically interconnected by a linkage member 82. The linkage member 80 may be provided so that ultrasound imager 50 and x-ray detector 40 may be selectively interconnected and disconnected (e.g. via mating engagement between complimentary shaft and cylinder members provided on the radiation detector 40 and ultrasound imager 50, respectively). In another arrangement, two separate bracket members may be interconnected to pendulum member 27 for separate interconnection to x-ray detector 40 and ultrasound imager 50, respectively. In yet another approach, a single bracket member may be utilized, wherein the x-ray detector 40 and ultrasound imager 50 may be separately disconnected/interconnected thereto for sequential imaging operations.

To accommodate x-ray imaging operations, the compression member 28 should be radiolucent. For example, a low density, thermoplastic material may be employed. The support layer 36 of housing 32 should be both radiolucent and sonolucent. For example, a low-density thermoplastic having a relatively small x-ray attenuation coefficient may be employed. In one arrangement, a crystalline, or aliphatic, polymer may be utilized, such as a poly 4-methyl, 1-pentene (i.e. PMP) material, e.g. a material commercially available under the product name "TPX" from Mitsui Plastics, Inc., White Plains, N.Y.

As will be further described, ultrasound imager 50 may comprise an ultrasound transducer 52 that transmits and receives ultrasound signals. To facilitate ultrasound operations, the ultrasound transducer 52 may be acoustically coupled to a bottom side of the support layer 36 via an acoustic coupling means 54. Further, an acoustic coupling means 56 may be utilized to acoustically couple a patient's breast 100 to a topside of support layer 36. For example, a standard ultrasound gel (e.g. a glycerin-based gel) gel or other flowable acoustic couplant may be contained within a pad located in contact with or otherwise applied to either or both of the top and bottom sides of support layer 36. Alternatively, acoustic coupling means 56 may comprise an ultrasound-coupling, solid-disposable membrane, e.g. a SCANTAC membrane offered by Sonotech, Inc. of Bellingham, Wash. As may be appreciated, the use of a gel-containing pad or solid-membrane for acoustic coupling means 56 may reduce or even avoid the need to apply ultrasound couplants directly to a patient's breast 100, thereby reducing:set-up and clean-up procedures.

Figure 3A:
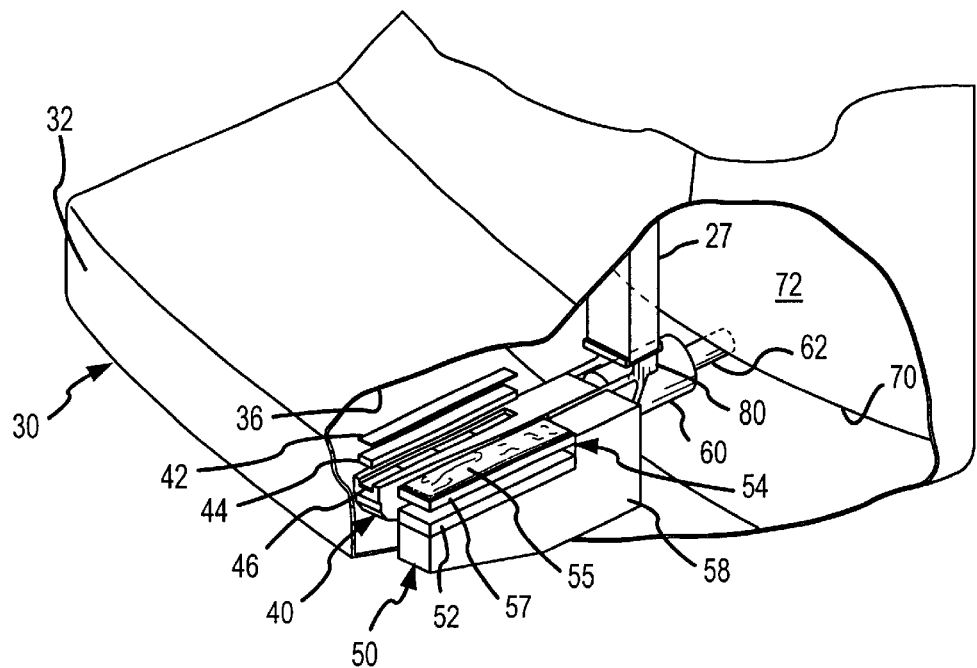
FIG. 3A is a perspective cutaway and partial exploded assembly view of one imaging assembly embodiment of the system embodiment of FIG. 1.
Figure 3B:
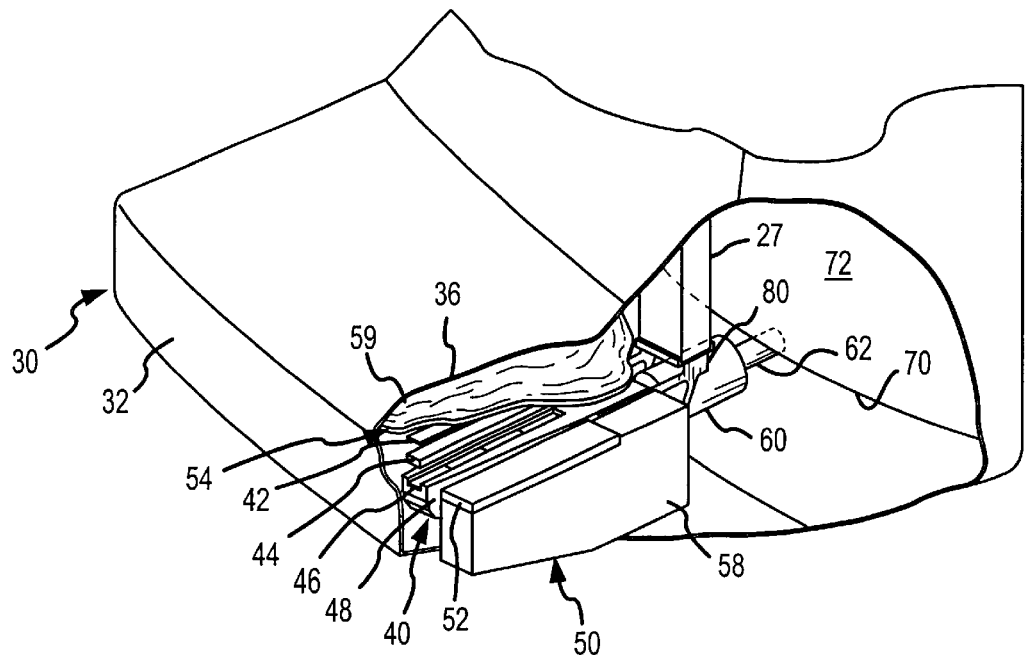
FIG. 3B is a perspective cutaway and partial exploded assembly view of another imaging assembly embodiment of the system embodiment of FIG. 1.

Reference is now made to the partial exploded assembly views of FIGS. 3A and 3B. As illustrated, x-ray detector 40 may include a light scintillator 42 (e.g. comprising a cesium iodide material), a fiber optic plate 44 and a plurality of abutting, charged coupled devices (CCDs) 46. When assembled, such components may be disposed in adjacent, contact relation on a support member 48 that is interconnected or interconnectable to a support bracket 80 that is interconnected or interconnectable to/disconnectable from the bottom end of pendulum member 27. As shown, drive motor 60 may also be interconnected to pendulum member 27 via support bracket 80. As may be appreciated, scintillator 42 produces light in response to the receipt of radiation signal 26. In turn, such light may be coupled via fiber optic plate 44 to a top surface of the CCDs 46 for detection and signal generation.

In the later regard, the CCDs 46 may each comprise an array of light sensitive elements. In one arrangement, each CCD has a 405×2048 array of 27-micron pixels. The CCDs may be operated in a time delay integration (TDI) mode, wherein electronic charge is accumulated and shifted from row-to-row and readout in synchronicity with, but in a direction opposite to, the scanning movement travel path of the x-ray detector 40. In turn, the resultant radiation image signal may be digitized for storage, processing and image display at monitoring station 10.

Numerous other x-ray detector arrangements may be utilized. For example, such arrangements may include detectors which utilize a light scintillator, photodiodes and thin film transistor (TFT) readout; or detectors employing direct conversion, voltage potential and TFT readout.

With further reference to FIGS. 3A and 3B, it can be seen that the ultrasound transducer 52 may be carried by a support member 58. Support member 58 may be interconnected or interconnectable to/disconnectable from the support member 48 of radiation detector 40, e.g. by the linkage member 82 of FIGS. 2A–2C. In one alternate arrangement, the support member 58 may be separately interconnected or interconnectable to/disconnectable from the pendulum member 27 via a modified or separate support bracket 80.

The ultrasound transducer 52 may comprise an array of ultrasound transducer elements. For example, a plurality of transducer elements with crystals operative in a 7.5–10 MHz frequency range may be employed. As will be appreciated, the ultrasound transducer 52 may transmit/receive an ultrasound signal during pulse/echo operations, wherein a resultant ultrasound image may be output and digitized for storage, processing and image display at monitoring station 10.

The array of ultrasound transducer elements comprising ultrasound transducer 52 may be disposed in parallel relation to the above-noted array of light sensitive elements comprising CCDs 46. More particularly, the support members 48,58 may be provided for interconnection therebetween and/or for separate interconnection to drive means such as drive motor 60, wherein the orientation of the array of light sensitive elements of CCDs 46 is the same as the orientation of the array of transducer elements of ultrasound transducer 52 relative to their respective scanning travel paths and the imaging frame of reference in which a selected body region is positioned (e.g. array rows/columns are parallel/perpendicular to the scanning paths). As such, regardless of whether x-ray and ultrasound imaging occur simultaneously, in overlapping fashion, or sequentially, the corresponding images may be readily registered in relation to the imaging frame of reference.

As may be appreciated, the array of light sensitive elements comprising CCDs 46, and the array of ultrasound transducer elements comprising ultrasound transducer 52, may each be of a corresponding width that is less than a width of a selected body region to be imaged. In turn, and by virtue of the scanning movement of the x-ray detector 40 and ultrasound imager 50 relative to the selected body region, the corresponding x-ray image and ultrasound image signals may be processed to yield full-field images of the selected body region. Further in this regard, it may be appreciated that the array of light sensitive elements comprising CCDs 46, and the array of ultrasound transducer elements comprising ultrasound transducer 52, may each be of a corresponding length that is greater than the length of a selected body region to be imaged (e.g the anterior-to-posterior dimension of a patient's breast 100 in FIGS. 2A–2C), wherein x-ray imaging and ultrasound imaging of the selected body region can each be achieved via a single scanning movement of the x-ray detector 40 and ultrasound imager 50, respectively. Alternatively, either or both of the x-ray detector 40 and ultrasound imager 50 may be of a lesser length; e.g. the array of ultrasound transducer 52 may be of a lesser length, wherein the ultrasound transducer 52 may be disposed for driven movement in a raster-like or return carriage manner for multi-pass imaging (e.g. via bi-directional or unidirectional scanning).

Referring now to the specific arrangement illustrated in FIG. 3A, an acoustic coupling means 54 is shown that includes a coupling pad 55 filled with a sonolucent flowable material (e.g. a hydrogel) located within a tray member 57 (e.g. comprising a sonolucent material), which in turn is positioned in direct contact with the ultrasound transducer 52. In operation, the coupling pad 55 slidably engages the bottom side of support layer 36 during ultrasound scanning operations. To facilitate such engagement, an acoustic lubricant (e.g. mineral oil) may be applied to the top of the coupling pad 55.

In the arrangement illustrated in FIG. 3B, an acoustic coupling means 54 is shown that comprises a coupling pad 59 filled with a sonolucent flowable material (e.g. a hydrogel) interconnected to and extending across the bottom side of support layer 36. In turn, ultrasound transducer 50 is disposed for sliding engagement with the coupling pad 59 during ultrasound scanning operations. To facilitate such engagement, an acoustic lubricant (e.g. mineral oil) may be applied to the top surface of the ultrasound transducer 52.

In addition the above-noted arrangements, further embodiments may employ varied structural relationships and additional componentry. For example, in some arrangements the ultrasound transducer 52 may be disposed and otherwise driven to follow a substantially linear travel path during scanning operations. Relatedly, support member 36 may be substantially planar, wherein the travel path for the ultrasound transducer 52 is substantially parallel to the plane defined by support layer 36. In such an arrangement, the x-ray detector 40 may be disposed within imaging assembly 30 to follow a substantially linear travel path or an arcuate travel path.

In another modified arrangement, the above-noted support member 58 may be modified to facilitate movement of the ultrasound transducer 52 toward and away from the support layer 36. More particularly, and by way of example, a modified bracket member 80 may be provided having a slot that extends normal to the bottom side of support layer 36 and within which support member 58 may be mounted for travel toward/away the support layer 36 along the slot. For example, the support member 58 may be spring-loaded, or biased, within the slot towards the support layer 36 so as to facilitate engagement therewith while also allowing for the above-noted sliding engagement between acoustic coupling pad 55 and support layer 36 (FIG. 3A) or between the ultrasound transducer 52 and acoustic coupling pad 59 (FIG. 3B).

Additionally, in a further modified arrangement, the support member 58 may be provided to allow a predetermined range of automatic pitch and/or attitude adjustment of ultrasound transducer 52. Such automatic adjustability may be provided to allow the face of the ultrasound transducer 52 to maintain an optimal interface via the acoustic coupling means 54 with support layer 36. By way of example, support member 58 may implement a ball-joint or gimbal arrangement which facilitates pivotal movement of the lateral and/or longitudinal axes (e.g. about a common center location) of the ultrasound transducer 52. Such arrangements may be particularly apt where support layer 36 is of a pliable construction since the orientation of the face of ultrasound transducer 52 may automatically adjust to accommodate local shape changes of the support layer 36 caused by variations in the compressed tissue region to imaged.

Figure 4:
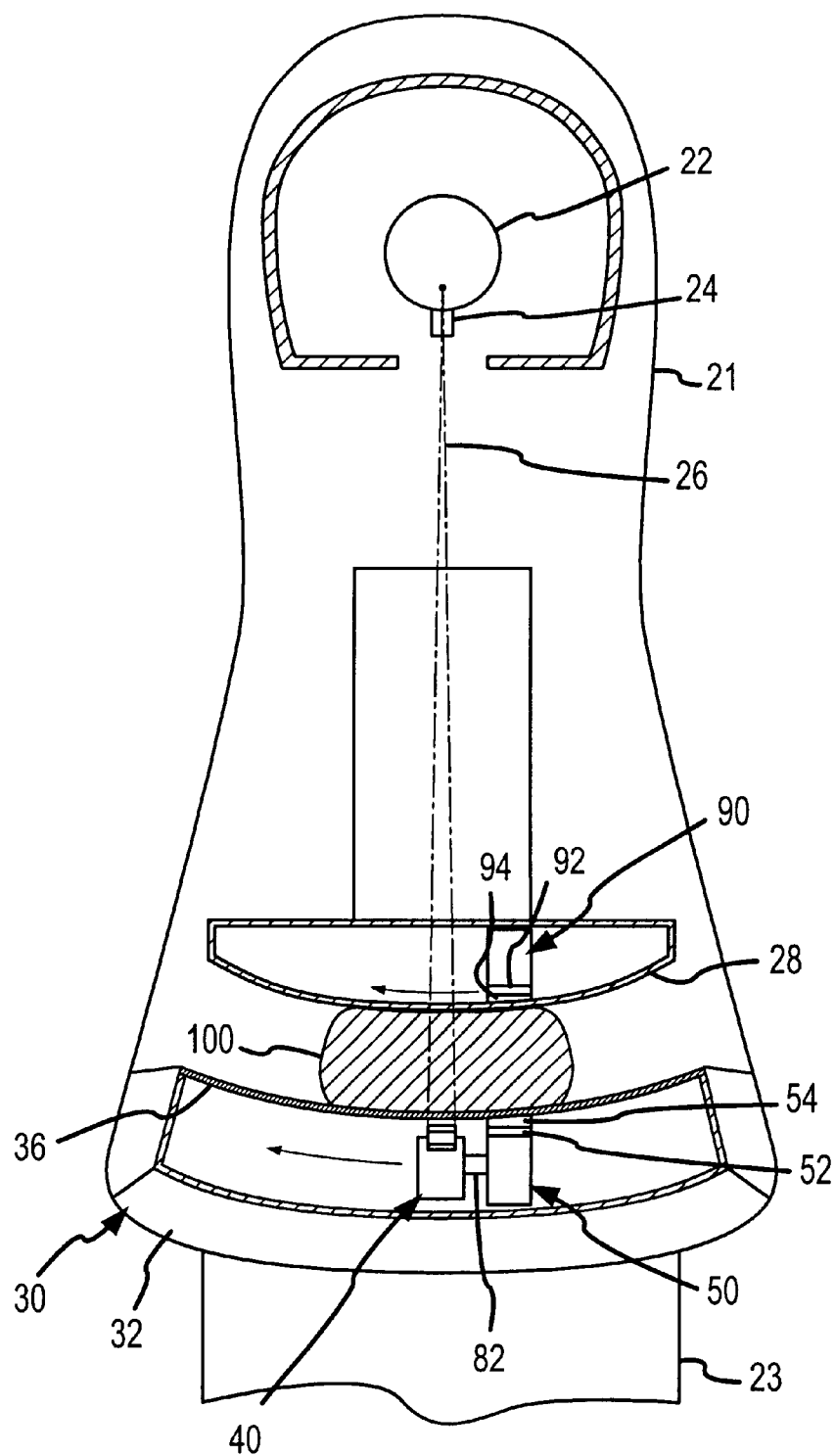
FIG. 4 is a cross-sectional front view of another embodiment of an imaging station comprising dual ultrasound transducers.

FIG. 4 illustrates a further embodiment of the present invention. Such embodiment may include the same features as described above in relation to the embodiment of FIG. 1 and FIGS. 2A–2C and FIGS. 3A and/or 3B, and further includes a second ultrasound imager 90. By way of example, the second ultrasound imager 90 may be positioned on a side of a patient's breast 100 that is opposite to the side on which the above-noted ultrasound transducer 50 is located. More particularly, the ultrasound imager 90 may be positioned in contact relation with a top surface of a sonolucent and radiolucent compression member 28. In turn, an ultrasound transducer 92 may provided with an acoustic coupling member 94 which directly engages the compression member 28. The ultrasound imager 90 may be interconnected to the above-noted pendulum member 27 so that ultrasound imagers 50 and 90 move in tandem and in opposing faceto-face relation during ultrasound imaging operations.

As may be appreciated, multiple ultrasound signals may be transmitted and/or received by the ultrasound imagers 50,90 to obtain enhanced ultrasound information. By way of example, the transmission and reception of ultrasound signals between the ultrasound imagers 50,90 may yield particular information pertaining to tissue attenuation and signal velocity.

Figure 5:
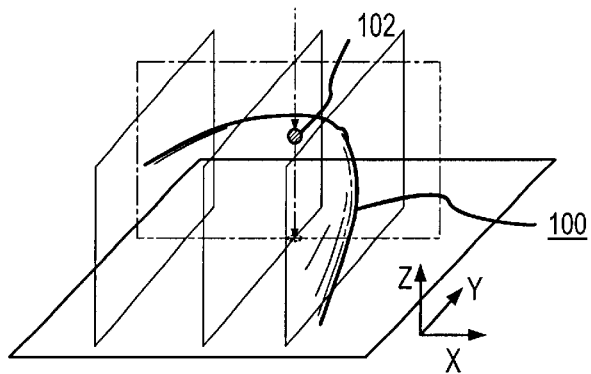
FIG. 5 illustrates an exemplary patient breast located within a predetermined imaging frame of reference and potential image plane views that may be generated.

Reference is now made to FIG. 5 which illustrates the positioning of a patient breast 100 within a predetermined frame of reference corresponding with the region located immediately adjacent to the support member 36 of the imaging assembly 30 of FIGS. 2A–2C. As will be appreciated, the image data comprising the image signal provided by x-ray detector 40 may be utilized to generate a projected XY plane image of the breast 100. The image data comprising the image signal provided by the ultrasound imager 50 may be utilized to generate YZ plane images, XZ plane images and XY plane images of the patient breast 100.

Figure 6A:
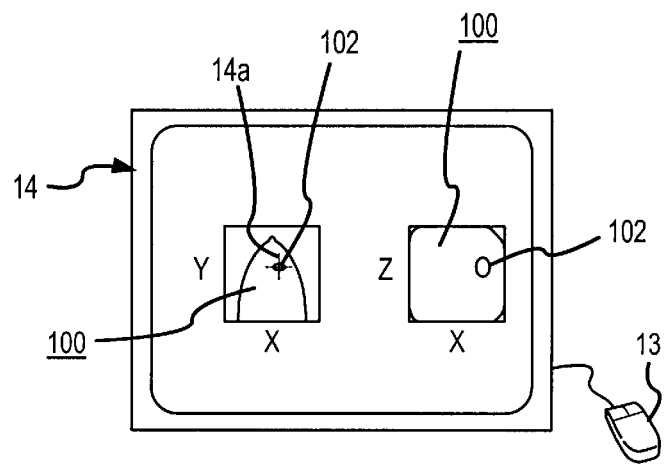
FIG. 6A illustrates an exemplary projected x-ray image and ultrasound image that may be displayed via use of the radiation image signal and ultrasound image signal obtained in various embodiments of the present invention.

Further in this regard, and as shown in FIG. 6A, a projected XY x-ray image and a selected XZ ultrasound image may be displayed at the display 14 of monitoring station 10. By way of example, a tissue region of interest 102 (e.g. a suspicious mass) may appear in a projected XY plane image. In turn, a user may utilize the input mouse 13 at monitoring station 10 to control the positioning of a display cursor 14a, wherein the cursor 14a may be located on the tissue region of interest 102 in the projected XY plane image. When the curser position is input via mouse 13 (e.g. by a button: click) the illustrated crosscut XZ plane image may be automatically displayed.

As may be appreciated, monitoring station 10 may be provided to permit enlargement of a selected region of a displayed image. For example, in addition to the illustrated cross-hair configuration of cursor 14a, cursor 14a may comprise a polygonal configuration (e.g. a square or rectangular configuration) that may be positioned to "frame" an enlarged area to be shown in the XZ ultrasound image.

Figure 6B:
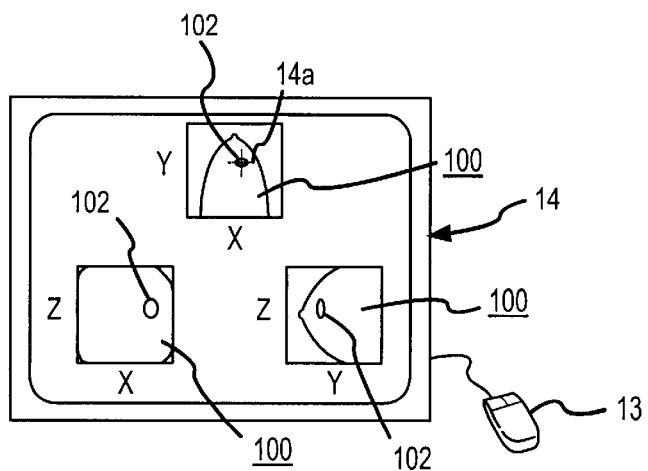
FIG. 6B illustrates various two-dimensional images that may be displayed via use of the radiation image signal and ultrasound image signal obtained in various embodiments of the present invention.

In another arrangement, and as shown in FIG. 6B, a projected XY x-ray image and selected XZ and YZ ultrasound images may be displayed at the display 14 of the monitoring station 10. Again, a user may employ the input mouse 13 to select a tissue region of interest 102, wherein the illustrated crosscut, XZ and ZY plane images may be automatically displayed. Then, the cursor 14a may be located on the tissue region of interest 102 on either of the XZ plane or ZY plane images, wherein input of the cursor position via mouse 13 may cause an XY plane image (not shown) in the corresponding Z plane to be generated/displayed via use of the ultrasound image data. The various displayable images may be enlarged or otherwise enhanced by processor 16 so as to further facilitate characterization of the tissue region of interest 102 by medical personnel.

Figure 7:
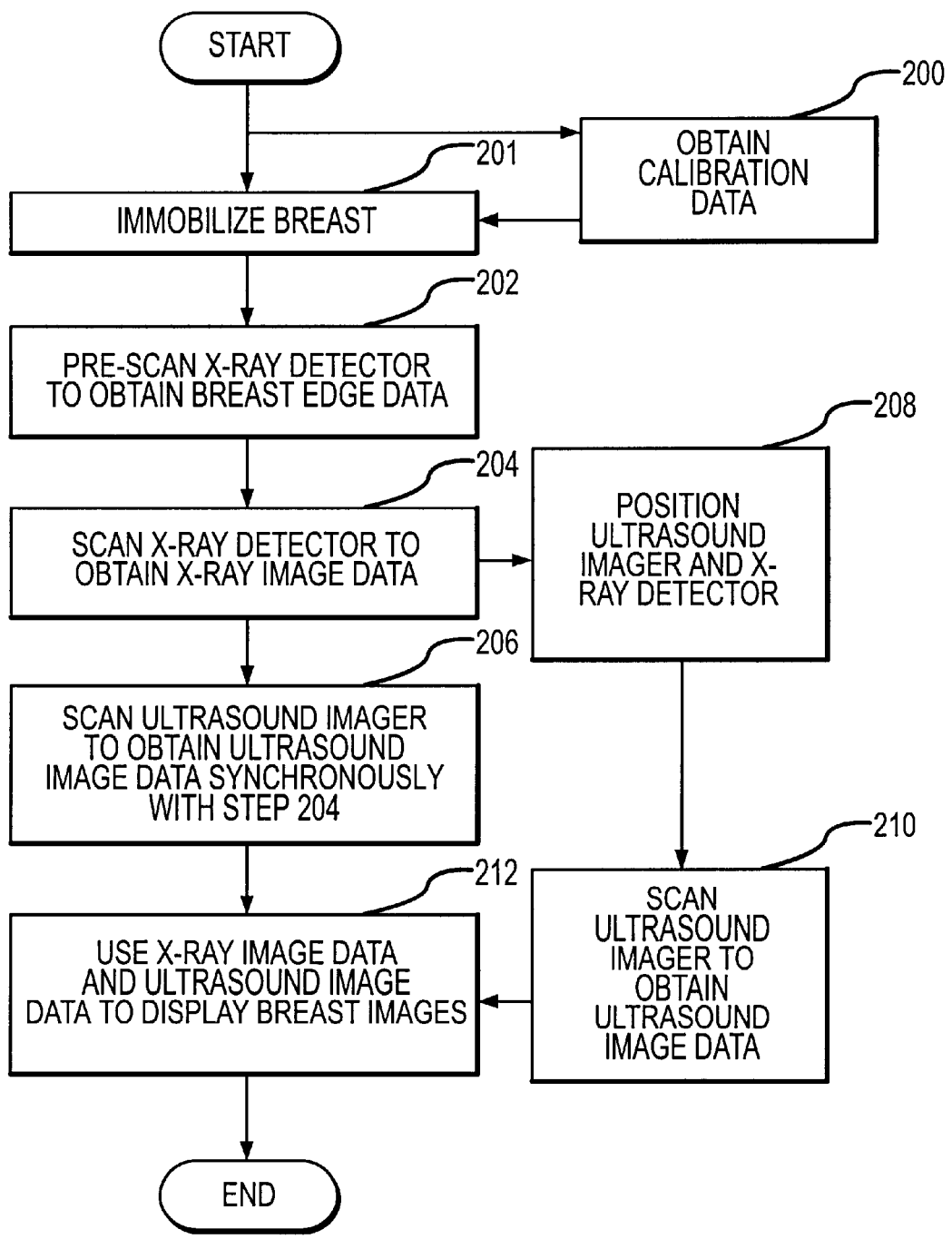
FIG. 7 is a high-leveled diagram showing various steps of method embodiments of the present invention.

Reference will now be made to FIG. 7, which illustrates general steps of method embodiments comprising the present invention. As shown, prior to a given imaging procedure, processor 16 may cause radiation signal 26 to be scanned across imaging assembly 30 together with driven scanning movement of x-ray detector 40 and ultrasound imager 50. As a result, corresponding calibration image signals may be provided for subsequent use in image processing (step 200), as will be noted below.

For patient screening, a patient breast 100 may be immobilized (step 201), e.g. the patient breast 100 may be located in contact relation with the support layer 36 of the imaging assembly 30. For such proposes, the upper member 21 may be raised/lowered/rotated as desired. Then, compression member 24 may be advanced towards the patient breast 100 so as to compress the patient breast 100 within the predetermined imaging frame of reference.

Next, processor 16 may cause a pre-scan to be completed by scanning radiation signal 26 and x-ray detector 40, wherein the resultant x-ray image signal may be processed to determine the location of the edges of the patient breast 100 within the predetermined imaging frame of reference (step 202). Optionally, a pre-scan image using ultrasound imager 50 alone may determine the edge of the breast and the composition of the breast, thus providing information for optimizing x-ray imaging exposure parameters. Such breast edge and additional information may be utilized in conjunction with subsequent imaging steps. For example, processor 16 may utilize the breast edge information so as to position the x-ray detector 40 at a location immediately adjacent to a breast edge for imaging.

In any case, after the optional pre-scan, the radiation source 22 and x-ray detector 40 may be controlled so as to scan the radiation signal 26 and x-ray detector 40 across the patient breast 100 in tandem, thereby obtaining a radiation image signal (step 204). In turn, the radiation image signal may be digitized and the resultant image data may be processed/stored/displayed at the monitoring station 10. In conjunction with such processing, calibration signal data obtained in step 200 may be employed.

In one embodiment, the method may further include the step of scanning the ultrasound imager 50 relative to the patient breast 100 (step 206) substantially synchronously with x-ray scanning (step 204). In turn, the signal may be digitized and the resultant image data ultrasound image may be processed/stored/displayed at the monitoring station 10. In conjunction with such processing, calibration signal data obtained in step 200 may be employed.

In another embodiment, x-ray imaging and ultrasound imaging may be completed sequentially. For example, after x-ray imaging (step 204) the ultrasound imager 50 may be positioned for imaging operations (step 208). More particularly, the x-ray detector 40 may be replaced by the ultrasound imager 50. Alternatively, the ultrasound imager 50 may be displaced from a retracted position to an advanced position relative to the support layer 36 of housing 32, wherein acoustic coupling means 54 only engages the bottom side of the support layer 36 when located in the advanced position.

In any case, once ultrasound imager 50 is properly positioned, the processor 16 may initiate ultrasound scanning operations (step 210), wherein the ultrasound imager 50 provides an ultrasound image signal to the processor 16 for image data storage/processing/display. Again, in conjunction with such processing, calibration signal data obtained in step 200 may be employed.

As shown by FIG. 7, the various methods may also provide for the selected display of x-ray and ultrasound images (step 212). For example, and as noted above, such data may be utilized to provide a projected XY plane image and selected XY, XZ and YZ plane images corresponding with a tissue region of interest identified by medical personnel. In turn, such images may be viewed, enhanced, etc. by medical personnel to characterize the tissue region of interest.

The embodiments described above are for exemplary purposes only and is not intended to limit the scope of the present invention. Various adaptations, modifications and extensions of the embodiment will be apparent to those skilled in the art and are intended to be within the scope of the invention as defined by the claims which follow.

What is claimed:

1. An apparatus for use in generating images of a selected region of a patient's body, comprising:

a radiation source for transmitting a radiation signal through a selected region of a patient's body;

radiation detection means, positionable for scanning movement along a first path, for receiving a portion of said radiation signal passing through a selected region of a patient's body during said scanning movement and providing a first image signal responsive thereto; and an ultrasound transducer, positionable for scanning movement along a second path, for receiving an ultrasound signal from a selected region of a patient's body during said second movement and providing a second image signal responsive thereto, wherein said second path is one of the same and substantially coincidental to said first path.

2. An apparatus as recited in claim 1, wherein a selected region of a patient's body is positionable so that said radiation source is on a first side thereof and said radiation detection means and said ultrasound transducer are both positioned on an opposing, second side thereof.

3. An apparatus as recited in claim 2, further comprising:

a support layer having a first side for contacting a selected region of a patient's body and an opposing second side, wherein said radiation detection means and said ultrasound transducer are both located adjacent to said second side of the supporting layer.

4. An apparatus as recited in claim 3, wherein said first side of the support layer is of an arcuate configuration.

5. An apparatus as recited in claim 4, wherein said first path is arcuate.

6. An apparatus as recited in claim 3, wherein said first side of the support layer is of a planar configuration.

7. An apparatus as recited in claim 6, wherein said second path is linear.

8. An apparatus as recited in claim 1, further comprising:

processor means for controlling operation of said radiation source, radiation detection means and ultrasound transducer, wherein said radiation detection means and said ultrasound transducer are controllable for at least partially overlapping imaging operations.

9. An apparatus as recited in claim 8, further comprising:

drive means for effecting co-scanning movement of said radiation detection means and said ultrasound transducer.

10. An apparatus as recited in claim 9, wherein said radiation detection means and said ultrasound transducer are interconnected in fixed relation to one another.

11. An apparatus as recited in claims 10, wherein one of said radiation detection means and said ultrasound transducer is supportably carried by the other.

12. An apparatus as recited in claim 1, wherein said radiation detection means is maintained at a substantially fixed distance from said radiation source throughout said scanning movement thereof.

13. An apparatus as recited in claims 1, wherein said radiation detection means comprises an array of detector elements and said ultrasound transducer comprises an array of transducer elements, and wherein said arrays are oriented in like relation relative to said first path and second path, respectively.

14. An apparatus as recited in claims 1, wherein at least one said radiation detection means and said ultrasound transducer is of a width that is less than a width of a selected region of a patient's body to be imaged.

15. An apparatus as recited in claims 1, wherein said radiation detection means and said ultrasound transducer have corresponding widths which are each less than a width of a selected region of a patient's body to be imaged.

16. An apparatus as recited in claims 15, wherein said radiation detection means and said ultrasound transducer have corresponding lengths which are each at least as great as a length of a selected region of a patient's body to be imaged.

17. An apparatus as recited in claim 1, further comprising:

a display for displaying a plurality of images of said selected body region generated using said first and second image signals; and, a user input for selecting a desired image by identifying a location of interest in a different image.

18. An apparatus as recited in claim 1, wherein a pair of ultrasound transducers are positionable for scanning movement along substantially parallel paths, wherein one of said pair is located on a first side of said selected body region and the other of said pair is located on an opposing second side of said selected body region.

19. A method for use in obtaining image data for a selected region of a patient's body, comprising:

transmitting a radiation signal from a radiation source through a selected region of a patient's body;

moving a radiation detection means along a first path during said transmitting step, wherein said radiation detection means receives a portion of said radiation signal passing through a selected region of a patient's body and provides a first image signal responsive thereto; and, displacing an ultrasound transducer along a second path that is one of the same and substantially coincidental to said first path, wherein said ultrasound transducer receives an ultrasound signal from said selected region of a patient's body and provides a second image signal responsive thereto.

20. A method as recited in claim 19, further comprising:

immobilizing said selected region of a patient's body within a predetermined frame of reference, wherein said transmitting, moving and displacing steps are completed during said immobilizing step.

21. A method as recited in claim 20, wherein said mobilizing step includes:

compressing said selected region of a patient's body.

22. A method as recited in claim 19, wherein said radiation source is located on a first side of said selected body region and said radiation detection means and said ultrasound transducer are both positioned on an opposing second side thereof.

23. A method as recited in claim 19, wherein said moving and displacing steps at least partially overlap.

24. A method as recited in claim 23, wherein said moving and displacing steps are completed in substantial synchronicity.

25. A method as recited in claim 19, wherein said moving and displacing steps are completed sequentially.

26. A method as recited in claim 19, wherein said ultrasound transducer transmits said ultrasound signal into said selected body region during said displacing step.

27. A method as recited in claim 19, wherein said displacing step includes:

displacing a pair of ultrasound transducers along substantially parallel paths, wherein one of said pair is located on a first side of said selected body region and the other of said pair is located on an opposing second side of said selected body region, and wherein said pair provide second image signals.

28. A method as recited in claim 19, further comprising:

selecting a desired image for display by identifying a location of interest in a different displayed image.

\* \* \* \* \*

UNITED STATES PATENT AND TRADEMARK OFFICE
CERTIFICATE OF CORRECTION

PATENT NO. : 6,846,289 B2
DATED : January 25, 2005
INVENTOR(S) : Besson et al.

It is certified that error appears in the above-identified patent and that said Letters Patent is hereby corrected as shown below:

Column 14,
Lines 47, 54, 60 and 64, delete "claims", and insert therefor -- claim --.

Column 15,
Line 1, delete "claims", and insert therefor -- claim --.

Column 16,
Lines 6 and 7, delete "mobilizing", and insert therefor -- immobilizing --.

Signed and Sealed this

Thirty-first Day of May, 2005

JON W. DUDAS
*Director of the United States Patent and Trademark Office*